(12) United States Patent
Dargazanli et al.

(10) Patent No.: US 7,326,722 B2
(45) Date of Patent: *Feb. 5, 2008

(54) N-[PHENYL(PIPERIDIN-2-YL)METHYL]BENZAMIDE DERIVATIVES, THEIR PREPARATION AND THEIR APPLICATION IN THERAPY

(75) Inventors: Gihad Dargazanli, Cachan (FR); Geneviève Estenne-Bouhtou, Chevilly-Larue (FR); Pascale Magat, Chilly-Mazarin (FR); Benoît Marabout, Massy (FR); Florence Medaisko, Saint Maur des Fosses (FR); Pierre Roger, Montigny-le-Bretonneux (FR); Mireille Sevrin, Paris (FR); Corinne Veronique, Antony (FR)

(73) Assignee: Sanofi-Aventis, Paris (FR)

( * ) Notice: Subject to any disclaimer, the term of this patent is extended or adjusted under 35 U.S.C. 154(b) by 83 days.

This patent is subject to a terminal disclaimer.

(21) Appl. No.: 10/511,886

(22) PCT Filed: Apr. 17, 2003

(86) PCT No.: PCT/FR03/01232

§ 371 (c)(1),
(2), (4) Date: Oct. 19, 2004

(87) PCT Pub. No.: WO03/089411

PCT Pub. Date: Oct. 30, 2003

(65) Prior Publication Data
US 2005/0159450 A1    Jul. 21, 2005

(30) Foreign Application Priority Data
Apr. 19, 2002  (FR) .................................. 02 04916

(51) Int. Cl.
  *A61K 31/445*  (2006.01)
  *C07D 413/02*  (2006.01)
(52) U.S. Cl. ............... 514/331; 544/126; 546/186; 546/207; 546/234
(58) Field of Classification Search ............ 546/247, 546/186, 207, 234; 514/331; 544/126
See application file for complete search history.

(56) References Cited

U.S. PATENT DOCUMENTS 5,524,569 A    6/1996  Rich et al.

FOREIGN PATENT DOCUMENTS

| EP | 0499995 | 8/1992 |
| WO | WO99/45011 | 9/1999 |
| WO | WO01/81308 | 11/2001 |

OTHER PUBLICATIONS

Caulfield et al., J. Med. Chem., 20001, 44, 2679-2682.*
Daneman et al., Cell, 2005, 123, 9-12.*
LeBowitz, PNAS, 2005, 102, 14485-14486.*
Lopez-Corcuera et al., Mol. Mem. Bio., 2001, 18, 13-20.*
Optical Isomers, Newton BBS, Jan. 23, 2006, Newton.dep.anl.gov.*
Woods et al. "Method of treating schizophrenia prodrome" CA 145:432223 (2006) (see copy in U.S. Appl. No. 11/045,247).*

* cited by examiner

*Primary Examiner*—Celia Chang
(74) *Attorney, Agent, or Firm*—Balaram Gupta

(57) ABSTRACT

The present invention discloses and claims a compound of general formula (I)

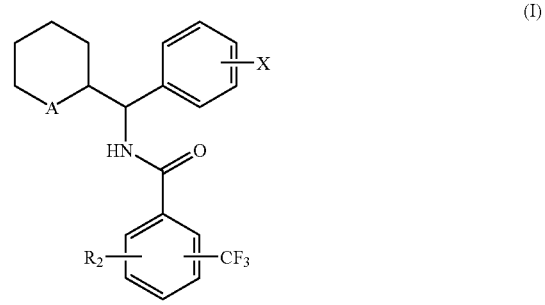

wherein A, X and $R_2$ are as described herein. Also disclosed and claimed is application of this compound in a variety of therapeutic applications.

19 Claims, No Drawings

N-[PHENYL(PIPERIDIN-2-YL)METHYL]BENZAMIDE DERIVATIVES, THEIR PREPARATION AND THEIR APPLICATION IN THERAPY

The compounds of the invention correspond to the general formula (I)

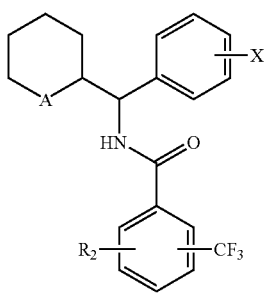

(I)

in which A represents either a group of general formula N—$R_1$ in which $R_1$ represents either a hydrogen atom, or a linear or branched ($C_1$–$C_7$)alkyl group optionally substituted with one or more fluorine atoms, or a ($C_4$–$C_7$)cycloalkyl group, or a ($C_3$–$C_7$)cycloalkyl($C_1$–$C_3$)alkyl group, or a phenyl($C_1$–$C_3$)alkyl group optionally substituted with one or two hydroxyl or methoxy groups, or a ($C_2$–$C_4$)alkenyl group, or a ($C_2$–$C_4$)alkynyl group, or a group of general formula $N^+(O^-)R_1$ in which $R_1$ is as defined above, or alternatively a group of general formula $N^+(R')R_1$ in which R' represents a linear or branched ($C_1$–$C_7$)alkyl group and $R_1$ is as defined above, X represents a hydrogen atom or one or more substituents chosen from halogen atoms and trifluoromethyl, linear or branched ($C_1$–$C_4$)alkyl and ($C_1$–$C_4$)alkoxy groups, $R_2$ represents either a hydrogen atom, or one or more substituents chosen from halogen atoms and trifluoromethyl, ($C_1$–$C_4$)alkyl or ($C_1$–$C_4$)alkoxy groups, or amino groups of general formula $NR_3R_4$ in which $R_3$ and $R_4$ each represent, independently of each other, a hydrogen atom or a ($C_1$–$C_4$) alkyl group, or form with the nitrogen atom carrying them a pyrrolidine, piperidine or morpholine ring, or a phenyl group optionally substituted with an atom or a group as defined for the symbol X above.

The compounds of general formula (I) may exist in the form of the threo racemate (1R,2R; 1S,2S) or in the form of enantiomers (1R,2R) or (1S,2S); they may exist in the form of free bases or of addition salts with acids.

Compounds having a structure which is analogous to that of the compounds of the invention are described in U.S. Pat. No. 5,254,569 as analgesics, diuretics, anticonvulsants, anaesthetics, sedatives, cerebroprotective agents, by a mechanism of action on the opiate receptors. Other compounds having an analogous structure are described in Patent Application EP 0499995 as 5-$HT_3$ antagonists which are useful in the treatment of psychotic disorders, neurological diseases, gastric syndromes, nausea and vomiting.

The compounds of the invention exhibit a particular activity as specific inhibitors of the glycine transporters glyt1 and/or glyt2.

The compounds preferred as inhibitors of the glyt1 transporter are of the configuration (1S,2S) with $R_2$ representing one or more halogen atoms or trifluoromethyl groups, while the compounds preferred as inhibitors of the glyt2 transporter are of the configuration (1R,2R) with $R_2$ representing a halogen atom and an amino group of general formula $NR_3R_4$.

The compounds of general formula (I) in which A represents a group of general formula N—$R_1$, where $R_1$ is different from a hydrogen atom, may be prepared by a method illustrated by scheme 1 which follows.

Scheme 1

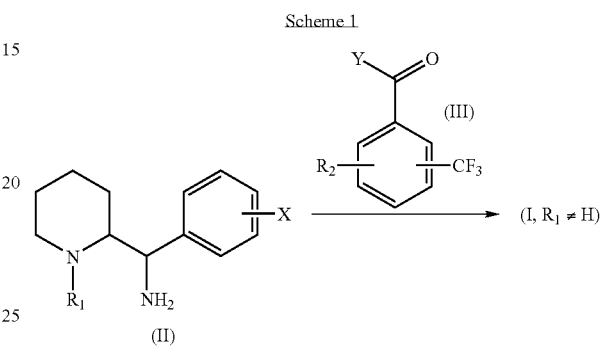

A diamine of general formula (II), in which $R_1$ and X are as defined above (with $R_1$ different from a hydrogen atom), is coupled to an activated acid or an acid chloride of general formula (III) in which Y represents a leaving group such as a halogen atom and $R_2$ is as defined above, using methods known to persons skilled in the art.

The diamine of general formula (II) may be prepared by a method illustrated by scheme 2 which follows.

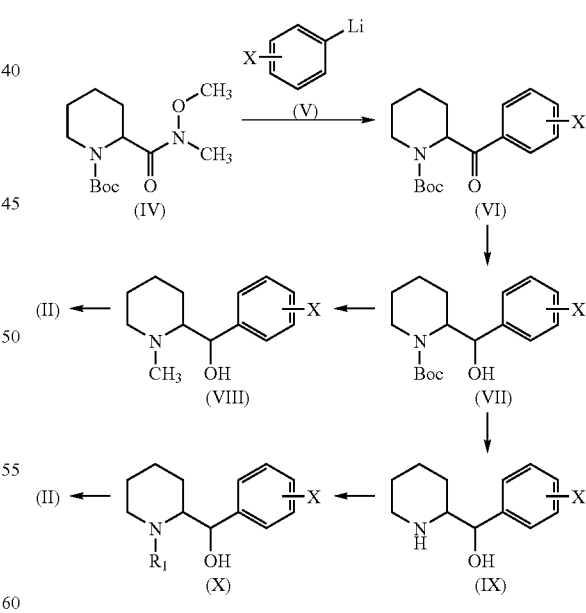

The Weinreb amide of formula (IV) is reacted with the phenyllithium derivative of general formula (V), in which X is as defined above, in an ethereal solvent such as diethyl ether, between −30° C. and room temperature; a ketone of general formula (VI) is obtained which is reduced to an alcohol with the threo configuration of general formula (VII)

with a reducing agent such as K-Selectride® or L-Selectride® (potassium or lithium tri-sec-butylborohydride), in an ethereal solvent such as tetrahydrofuran, between −78° C. and room temperature. The carbamate of general formula (VII) may then be reduced to a threo N-methylaminoalcohol of general formula (VIII) by the action of a mixed hydride such as lithium aluminium hydride, in an ethereal solvent such as tetrahydrofuran, between room temperature and the reflux temperature. The threo alcohol of general formula (VIII) is then converted to a threo intermediate of general formula (II) where $R_1$ represents a methyl group, in two steps: the alcohol functional group is first of all converted to a leaving group, for example a methanesulphonate group, by the action of methylsulphonyl chloride, in a chlorinated solvent such as dichloromethane, and in the presence of a base such as triethylamine, between 0° C. and room temperature, and then the leaving group is reacted with liquefied ammonia at −50° C., in an alcohol such as ethanol, in a closed medium such as an autoclave, between −50° C. and room temperature.

It is also possible to deprotect the carbamate of general formula (VII) by means of a strong base such as aqueous potassium hydroxide, in an alcohol such as methanol in order to obtain the threo amino alcohol of general formula (IX), and to then carry out an N-alkylation by means of a halogenated derivative of formula $R_1Z$, in which $R_1$ is as defined above, but different from a hydrogen atom, and Z represents a halogen atom, in the presence of a base such as potassium carbonate, in a polar solvent such as N,N-dimethylformamide, between room temperature and 100° C. The alcohol of general formula (X) thus obtained is then treated as described for the alcohol of general formula (VIII).

Another variant method, illustrated by scheme 3 which follows, may be used in the case where $R_1$ represents a methyl group and X represents a hydrogen atom. The pyridine oxime of formula (XI) is quaternized, for example, by the action of methyl trifluoromethanesulphonate, in an ethereal solvent such as diethyl ether, at room temperature. The pyridinium salt thus obtained, of formula (XII), is then subjected to hydrogenation under a hydrogen atmosphere, in the presence of a catalyst such as platinum oxide, in a mixture of an alcohol and an aqueous acid such as ethanol and 1 N hydrochloric acid. The diamine of general formula (II) is obtained in which $R_1$ represents a methyl group and X represents a hydrogen atom in the form of a mixture of the two diastereoisomers threo/erythro 9/1. It is possible to salify it, for example, with oxalic acid, and then to purify by recrystallization of the oxalate formed from a mixture of an alcohol and an ethereal solvent such as methanol and diethyl ether, so as to obtain the pure threo diastereoisomer (1R,2R; 1S,2S).

The compounds of general formula (I) in which A represents a group of general formula $NR_1$ where $R_1$ represents a hydrogen atom may be prepared by the method illustrated by scheme 4 which follows.

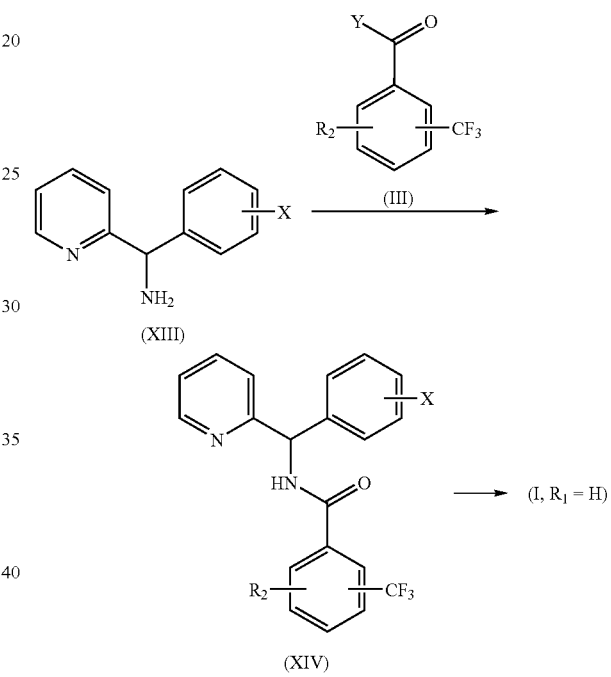

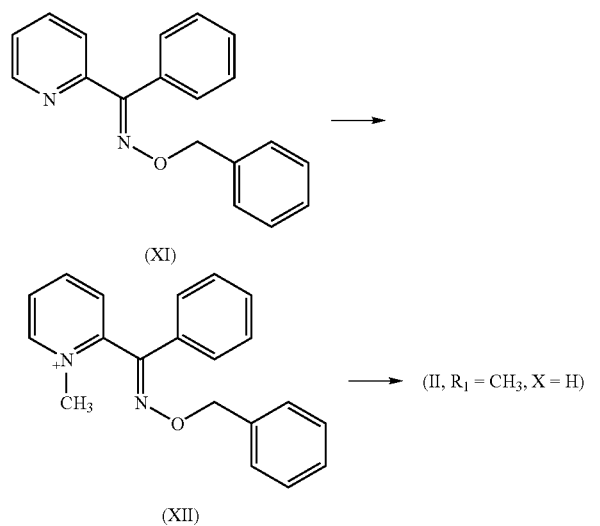

Starting with the amine of general formula (XIII), in which X is as defined above, a coupling is performed with an activated acid or an acid chloride, as described above, of general formula (III) according to methods known to persons skilled in the art, in order to obtain the compound of general formula (XIV). Finally, hydrogenation of the latter is performed, for example with hydrogen in the presence of a catalyst such as 5% platinum on carbon, in an acidic solvent such as glacial acetic acid, so as to finally obtain a compound of general formula (I) in which $R_1$ represents a hydrogen atom.

Another method consists, according to scheme 2, in using a compound of general formula (I) in which $R_1$ represents either an optionally substituted phenylmethyl group, and in deprotecting the nitrogen of the piperidine ring, for example, with an oxidizing agent or with a Lewis acid such as boron tribromide, or by hydrogenolysis, or an alkenyl group, preferably an allyl group, followed by deprotection with a $Pd^0$ complex, in order to obtain a compound of general formula (I) in which $R_1$ represents a hydrogen atom.

The compounds of general formula (I) in which A represents a group of general formula $N^+(O^-)R_1$ may be prepared from the compounds of general formula (I) in which A represents a group of general formula N—$R_1$, in which $R_1$ is as described above, by reaction with an oxidizing agent, for example 3-chloroperbenzoic acid, in a chlorinated solvent such as dichloromethane, at a temperature between 0° C. and room temperature.

The compounds of general formula (I) in which A represents a group of general formula $N^+(R')R_1$ may be prepared from compounds of general formula (I) in which A represents a group of general formula N—$R_1$ by reaction with an alkyl halide of general formula R'-Z, in which R' is as defined above and Z represents a halogen atom, in a polar solvent such as acetonitrile, at a temperature between room temperature and 100° C.

Moreover, the chiral compounds of general formula (I) corresponding to the enantiomers (1R,2R) or (1S,2S) of the threo diastereoisomer may also be obtained by separating the racemic compounds by high-performance liquid chromatography (HPLC) on a chiral column, or by resolution of the racemic amine of general formula (II) with the use of a chiral acid, such as tartaric acid, camphorsulphonic acid, dibenzoyltartaric acid, N-acetylleucine, by fractional and preferential recrystallization of a diastereoisomeric salt from an alcohol type solvent, or by enantioselective synthesis according to scheme 2, with the use of a chiral Weinreb amide of general formula (IV).

The racemic or chiral Weinreb amide of formula (IV) may be prepared according to a method similar to that described in *Eur. J. Med. Chem.*, 35, (2000), 979–988 and *J. Med. Chem.*, 41, (1998), 591–601. The phenyllithium compound of general formula (V) where X represents a hydrogen atom is commercially available. Its substituted derivatives may be prepared according to a method similar to that described in *Tetra. Lett.*, 57, 33, (1996), 5905–5908. The pyridine oxime of formula (XI) is prepared according to a method similar to that described in Patent Application EP-0366006. The amine of general formula (IX) in which X represents a hydrogen atom may be prepared in a chiral series according to a method described in U.S. Pat. No. 2,928,835. Finally, the amine of general formula (XIII) may be prepared according to a method similar to that described in *Chem. Pharm. Bull.*, 32, 12, (1984), 4893–4906 and *Synthesis*, (1976), 593–595.

The acids and acid chlorides of general formula (III) are commercially available, except in the case of 4-amino-3-chloro-5-trifluoromethylbenzoic acid. It is possible to prepare the latter by chlorination of 4-amino-5-trifluoromethylbenzoic acid with sulphuryl chloride, in a chlorinated solvent such as chloroform, according to a method similar to that described in *Arzneim. Forsch.*, 34, 11a, (1984), 1668–1679.

The examples which follow illustrate the preparation of a few compounds of the invention. The elemental microanalyses and the IR and NMR spectra and the HPLC on a chiral column confirm the structures and the enantiomeric purities of the compounds obtained.

The numbers indicated in brackets in the headings of the examples correspond to those of the 1st column of the table given later.

In the names of the compounds, the dash "-" forms part of the word, and the dash "_" only serves for splitting at the end of a line; it is suppressed in the absence of splitting, and should not be replaced either by a normal dash or by a gap.

EXAMPLE 1

(Compound No. 33)

threo-2-Chloro-N-[(1-ethylpiperidin-2-yl)phenylmethyl]-3-trifluoromethylbenzamide hydrochloride 1:1.

1.1. 1,1-Dimethylethyl 2-benzoylpiperidine-1-carboxylate 8.0 g (29.4 mmol) of 1,1-dimethylethyl 2-(N-methoxy-N-methylcarbamoyl)piperidine-1-carboxylate in 100 ml of anhydrous diethyl ether are introduced into a 250 ml round-bottomed flask, under an argon atmosphere, the medium is cooled to −25° C., 16 ml (29.4 mmol) of a 1.8 M solution of phenyllithium in a 70/30 mixture of cyclohexane and diethyl ether are added dropwise and the stirring is maintained for 2 h.

After hydrolysis with a saturated aqueous sodium chloride solution, the aqueous phase is separated, it is extracted with ethyl acetate, the organic phase is dried over sodium sulphate, it is filtered and the filtrate is concentrated under reduced pressure and the residue is purified by chromatography on a silica gel column, eluting with a mixture of ethyl acetate and cyclohexane.

2 g of a white solid are obtained.

1.2. 1,1-Dimethylethyl threo-[hydroxy(phenyl)methyl]piperidine-1-carboxylate.

2.0 g (6.9 mmol) of 1,1-dimethylethyl 2-benzoylpiperidine-1-carboxylate in 30 ml of anhydrous diethyl ether are introduced into a 250 ml round-bottomed flask, under an argon atmosphere, the solution is cooled to −78° C., 20.7 ml (20.7 mmol) of a 1 M solution of lithium tri-sec-butylborohydride in diethyl ether are added dropwise and the stirring is maintained for 3 h.

The mixture is hydrolysed with 16 ml of water and 16 ml of a 35% aqueous hydrogen peroxide solution, and the mixture is allowed to return to room temperature while it is being stirred for 2 h.

It is diluted with water and ethyl acetate, the aqueous phase is separated and is extracted with ethyl acetate. After washing the combined organic phases, drying over sodium sulphate and evaporation of the solvent under reduced pressure, the residue is purified by chromatography on a silica gel column, eluting with a mixture of ethyl acetate and cyclohexane.

2.0 g of an oily product are obtained.

1.3. threo-Phenyl(piperidin-2-yl)methanol.

A solution of 2.0 g (6.9 mmol) of 1,1-dimethylethyl threo-[hydroxy(phenyl)methyl]piperidine-1-carboxylate in 40 ml of methanol is placed in a 250 ml round-bottomed flask, an aqueous potassium hydroxide solution prepared from 2 g of potassium hydroxide pellets and 20 ml of water is added and the mixture is heated under reflux for 2 h.

The mixture is cooled, the solvent is evaporated off under reduced pressure, water is added and the mixture is extracted several times with dichloromethane. After washing the combined organic phases, drying over magnesium sulphate, filtration and evaporation of the solvent under reduced pressure, 1 g of a white solid is obtained.

Melting point: 172–174° C.

1.4. threo-(1-Ethylpiperidin-2-yl)phenylmethanol.

A solution of 1 g (5.2 mmol) of threo-phenyl(piperidin-2-yl)methanol in 30 ml of anhydrous N,N-dimethylformamide is placed in a 100 ml round-bottomed flask, 0.39 ml (5.2 mmol) of bromoethane and 0.8 g (5.8 mmol) of potassium carbonate are added and the mixture is heated at 80° C. for 2 h. It is cooled to room temperature, it is hydrolysed by adding water and it is extracted several times with ethyl acetate. After washing the combined organic phases with water and then a saturated aqueous sodium chloride solution, drying over magnesium sulphate, filtration and evaporation of the solvent under reduced pressure, the residue is purified by chromatography on a silica gel column, eluting with a mixture of dichloromethane and methanol. 0.8 g of an oily compound is obtained.

1.5. threo-(1-Ethylpiperidin-2-yl)phenylmethanamine.

0.8 g (3.65 mmol) of threo-(1-ethylpiperidin-2-yl)phenylmethanol and 0.48 ml (3.65 mmol) of triethylamine in 20 ml of anhydrous dichloromethane are introduced into a 100 ml round-bottomed flask, under an argon atmosphere, the mixture is cooled to 0° C., 0.28 ml (3.63 mmol) of methanesulphonyl chloride is added and the mixture is allowed to slowly return to room temperature for 2 h and it is concentrated under reduced pressure.

Liquefied ammonia is introduced into an autoclave provided with magnetic stirring and cooled to −50° C. and methanesulphonate prepared beforehand in solution in 10 ml of absolute ethanol is added, the autoclave is closed and the stirring is maintained for 48 h.

The mixture is transferred to a round-bottomed flask, it is concentrated under reduced pressure and the residue is purified by chromatography on a silica gel column, eluting with a mixture of dichloromethane and methanol.

0.3 g of an oily compound is obtained, which oily compound is used as it is in the next step.

1.6. threo-2-Chloro-N-[(1-ethylpiperidin-2-yl)phenylmethyl]-3-trifluoromethylbenzamide hydrochloride 1:1.

0.3 g (1.37 mmol) of 2-chloro-3-trifluoromethylbenzoic acid, 0.26 g (1.37 mmol) of 1-[3-(dimethylamino)propyl]-3-ethylcarbodiimide, and 0.19 g (1.37 mmol) of 1-hydroxybenzotriazole in solution in 10 ml of dichloromethane to a 50 ml round-bottomed flask and the mixture is stirred at room temperature for 30 min.

0.3 g (1.37 mmol) of threo-(1-ethylpiperidin-2-yl)phenylmethanamine in solutin in a few ml of dichloromethane is added and the stirring is continued for 5 h. The mixture is hydrolysed with water, and it is extracted several times with dichloromethane. After washing the organic phases with water and then with a 1 N aqueous sodium hydroxide solution, drying over magnesium sulphate, filtration and evaporation of the solvent under reduced pressure, the residue is purified by chromatography on a silica gel column, eluting with a mixture of dichloromethane and methanol.

0.25 g of an oily product are obtained.

The product is dissolved in a few ml of propan-2-ol, 5.9 ml of a 0.1 N hydrochloric acid solution in propan-2-ol are added, and the mixture is concentrated under reduced pressure in order to reduce the volume of the solvent. After trituration, 0.15 g of hydrochloride is finally isolated in the form of a white solid.

Melting point: 230–232° C.

EXAMPLE 2

(Compound No. 18)

2-Chloro-N-[(1S)-[(2S)-1-methylpiperidin-2-yl]phenylmethyl]-3-trifluoromethylbenzamide hydrochloride 1:1

2.1. 1,1-Dimethylethyl (2S)-2-benzoylpiperidine-1-carboxylate.

11.8 g (43.3 mmol) of 1,1-dimethylethyl (2S)-2-(N-methoxy-N-methylcarbamoyl)piperidine-1-carboxylate in 100 ml of anhydrous diethyl ether are introduced into a 500 ml round-bottomed flask, under a nitrogen atmosphere, the medium is cooled to −23° C., 21.6 ml (43.2 mmol) of a 1.8 M phenyllithium solution in a 70/30 mixture of cyclohexane and diethyl ether are added dropwise and the mixture is stirred at room temperature for 3 h.

After hydrolysis with a saturated aqueous sodium chloride solution, the aqueous phase is separated and it is extracted with ethyl acetate. The organic phase is dried over sodium sulphate, it is filtered, it is concentrated under reduced pressure and the residue is purified by chromatography on a silica gel column, eluting with a mixture of ethyl acetate and cyclohexane.

4.55 g of a solid product are obtained.

Melting point: 123–125° C. $[\alpha]_D^{25}$=−25.4° (c=2.22; $CH_2Cl_2$) ee=97.2%.

2.2. 1,1-Dimethylethyl (1S)-2-[(2S)-hydroxy(phenyl)methyl]piperidine-1-carboxylate.

4.68 g (16.2 mmol) of 1,1-dimethylethyl (2S)-2-benzoylpiperidine-1-carboxylate in 170 ml of anhydrous tetrahydrofuran are introduced into a 500 ml round-bottomed flask, under a nitrogen atmosphere, the solution is cooled to −78° C., 48.5 ml (48.5 mmol) of a 1 M solution of L-Selectride® (lithium tri-sec-butylborohydride) in tetrahydrofuran are added dropwise, and the mixture is stirred at room temperature for 5 h.

It is slowly hydrolysed in the cold state with 34 ml of water and 34 ml of a 35% aqueous hydrogen peroxide solution, and the mixture is allowed to return to room temperature while it is being stirred for 2 h.

It is diluted with water and ethyl acetate, the aqueous phase is separated, and it is extracted with ethyl acetate. After washing the combined organic phases, drying, drying over sodium sulphate, filtration and evaporation, the residue is purified by chromatography on a silica gel column, eluting with a mixture of ethyl acetate and cyclohexane.

4.49 g of a pale yellow oil are obtained.

$[\alpha]_D^{25}$=+63.75° (c=0.8; $CH_2Cl_2$) ee=97.8%.

2.3. (1S)-[(2S)-(1-methylpiperidin-2-yl)]phenylmethanol.

2.96 g (78.1 mmol) of lithium aluminium hydride in 50 ml of anhydrous tetrahydrofuran are introduced into a 200 ml two-necked flask, under a nitrogen atmosphere, the mixture is heated under reflux, 4.49 g (15.4 mmol) of a solution of 1,1-dimethylethyl (1S)-2-[(2S)-hydroxy(phenyl)methyl]piperidine-1-carboxylate in 35 ml of tetrahydrofuran are added and the mixture is kept under reflux for 3.5 h.

It is cooled, it is slowly hydrolysed with a 0.1 M solution of potassium sodium tartrate and the mixture is kept stirred overnight.

It is filtered and the precipitate is rinsed with tetrahydrofuran, and then the filtrate is concentrated under reduced pressure.

2.95 g of a colourless oily product are obtained.

2.4. (1S)-[(2S)-(1-methylpiperidin-2-yl)]phenylmethanamine.

2.95 g (14.4 mmol) of (1S)-[(2S)-(1-methylpiperidin-2-yl)]phenylmethanol and 2 ml (14.4 mmol) of triethylamine in 70 ml of anhydrous dichloromethane are introduced into a 250 ml round-bottomed flask, under a nitrogen atmosphere, the medium is cooled to 0° C., 1.1 ml (14.4 mmol) of methanesulphonyl chloride are added, the mixture is allowed to return slowly to room temperature over 2 h and it is concentrated under reduced pressure.

Liquefied ammonia is introduced into an autoclave provided with magnetic stirring and cooled to −50° C., a solution of crude methanesulphonate prepared beforehand in solution in 30 ml of absolute ethanol is added, the autoclave is closed and the stirring is maintained for 48 h.

The mixture is transferred to a round-bottomed flask and the amine is isolated in the form of an oily product which is used as it is in the next step.

2.5. 2-Chloro-N-[(1S)-[(2S)-1-methylpiperidin-2-yl]phenylmethyl]-3-trifluoromethylbenzamide hydrochloride 1:1.

Using the procedure described in point 1.6, starting with 1 g (4.9 mmol) of 2-chloro-3-trifluoromethylbenzoic acid, 0.9 g (4.9 mmol) of 1-[3-(dimethylamino)propyl]-3-ethylcarbodiimide hydrochloride, 0.66 g (4.6 mmol) of 1-hydroxybenzotriazole and 1 g (4.9 mmol) of (1S)-[(2S)-(1-methylpiperidin-2-yl)]phenylmethanamine, 0.45 g of product is obtained in base form after purification by chromatography on a silica gel column, eluting with a mixture of dichloromethane and methanol.

The product is dissolved in a few ml of propan-2-ol, 10.9 ml of a 1 N hydrochloric acid solution in propan-2-ol are added and the mixture is concentrated under reduced pressure in order to reduce the volume of solvent.

After trituration, 0.37 g of hydrochloride is finally isolated in the form of a white solid.

Melting point: 230–232° C. $[\alpha]_D^{25}$=+70.3° (c=0.825; $CH_3OH$) ee>99%.

EXAMPLE 3

(Compound No. 24)

threo-4-Amino-3-chloro-n-[(1-methylpiperidin-2-yl)phenylmethyl]-5-trifluoromethylbenzamide hydrochloride 1:1

3.1. 2-(Benzyloxyiminophenylmethyl)-1-methylpyridinium trifluoromethanesulphonate.

17.4 ml (120 mmol) of methyl trifluoromethanesulphonate are added dropwise and at 0° C. to a suspension of 35 g (120 mmol) of phenyl(pyridin-2-yl)methanone O-benzyloxime in 200 ml of diethyl ether, and the mixture is stirred at room temperature for 3 h.

The precipitate formed is recovered by filtration and it is dried under reduced pressure.

49 g of product are obtained, which product is used as it is in the next step.

3.2. threo-(1-Methylpiperidin-2-yl)phenylmethanamine ethanedioate 2:1.

14.8 g (31.89 mmol) of 2-(benzyloxyiminophenylmethyl)-1-methylpyridinium trifluoromethanesulphonate and 0.74 g of platinum oxide in 50 ml of ethanol and 50 ml of 1 N hydrochloric acid are placed in a Parr flask, and hydrogenation is performed for 5 h.

The ethanol is evaporated under reduced pressure, the residue is extracted with dichloromethane, the aqueous phase is separated, a solution of ammonia is added thereto and it is extracted with dichloromethane. After washing the combined organic phases, drying over sodium sulphate, filtration and evaporation of the solvent under reduced pressure, 6.7 g of an oily product comprising 10% of erythro diastereoisomer are obtained.

The ethanedioate is prepared by dissolving these 6.7 g of base in methanol, by the action of two equivalents of ethanedioic acid dissolved in the minimum of methanol.

The salt obtained is purified by recrystallization from a mixture of methanol and diethyl ether.

4.7 g of pure ethanedioate of the threo diastereoisomer are finally isolated.

Melting point: 156–159° C.

3.3. 4-Amino-3-chloro-5-trifluoromethylbenzoic acid.

7.8 g (40 mmol) of 4-amino-5-trifluoromethylbenzoic acid in 80 ml of chloroform are placed in a 500 ml round-bottomed flask in the presence of 9.97 ml (50 mmol) of sulphuryl chloride, and the mixture is stirred under reflux overnight.

The solvent is evaporated under reduced pressure, the residue is taken up in water and aqueous ammonia and the mixture is extracted with dichloromethane. The aqueous phase is acidified, the precipitate formed is recovered by filtration and it is dried under reduced pressure.

9 g of product are obtained.

Melting point: 229–235° C.

3.4. threo-4-Amino-3-chloro-N-[(1-methylpiperidin-2-yl)phenylmethyl]-5-trifluoromethylbenzamide hydrochloride 1:1.

0.52 g (2.15 mmol) of 4-amino-3-chloro-5-trifluoromethylbenzoic acid, 0.37 g (1.96 mmol) of 1-[3-(dimethylamino)propyl]-3-ethylcarbodiimide hydrochloride, 0.26 g (1.96 mmol) of 1-hydroxybenzotriazole in 5 ml of 1,2-dichloroethane are placed in a 100 ml round-bottomed flask, and the mixture is stirred at room temperature for 10 min. 0.4 g (1.96 mmol) of threo-(1-methylpiperidin-2-yl)phenylmethanamine in solution in 5 ml of 1,2-dichloroethane is added and the mixture is kept stirred for 12 h.

It is hydrolysed with water, potassium hydroxide pellets are added until a basic pH is obtained, and the mixture is extracted with dichloromethane. The organic phase is washed with water, it is dried over sodium sulphate, filtered, the solvent is evaporated under reduced pressure and the residue is purified by chromatography on a silica gel column, eluting with a mixture of dichloromethane and methanol.

0.4 g of compound is isolated in base form.

It is dissolved in a few ml of propan-2-ol, 9.4 ml of a 0.1 N hydrochloric acid solution in propan-2-ol are added and the solvent is evaporated under reduced pressure. The residue is collected and it is dried under vacuum.

0.285 g of solid product are obtained.

Melting point: 270–272° C.

EXAMPLE 4

(Compound No. 25)

4-Amino-3-chloro-N-[(1R)-[(2R)-1-methylpiperidin-2-yl]phenylmethyl]-5-trifluoromethylbenzamide hydrochloride 1:1

4.1. (1R)-[(2R)-(1-methylpiperidin-2-yl)]phenylmethanamine.

80 g (390 mmol) of threo-(1-methylpiperidin-2-yl)phenylmethanamine in solution in 300 ml of methanol and 68 g (390 mmol) of N-acetyl-D-leucine in solution in 450 ml of methanol are introduced into a 4 l round-bottomed flask. The solution is concentrated under reduced pressure and the residue is recrystallized from 1100 ml of propan-2-ol. 72 g of salts of (1R)-[(2R)-(1-methylpiperidin-2-yl)]phenylmethanamine are obtained.

The recrystallization is repeated three times and 15 g of a salt of (1R)-[(2R)-(1-methylpiperidin-2-yl)]phenylmethanamine are finally obtained.

Melting point: 171.5° C.

$[\alpha]_D^{25} = -11°$ (c=1; $CH_3OH$) ee>99%.

4.2. 4-Amino-3-chloro-N-[(1R)-[(2R)-1-methylpiperidin-2-yl]phenylmethyl]-5-trifluoromethylbenzamide hydrochloride 1:1.

Using the procedure described in point 3.4 above, starting with 1.04 g (4.37 mmol) of 4-amino-3-chloro-5-trifluoromethylbenzoic acid, 0.46 g (3.97 mmol) of 1-[3-(dimethylamino)propyl]-3-ethylcarbodiimide hydrochloride, 0.53 g (3.97 mmol) of 1-hydroxybenzotriazole and 1.5 g (3.97 mmol) of (1R)-[(2R)-methylpiperidin-2-yl]phenylmethanamine, 1.12 g of product are obtained in base form.

The hydrochloride thereof is prepared by adding 28.2 ml of a 0.1 N hydrochloric acid solution in propan-2-ol to a solution of 1.12 g of base in solution in a few ml of propan-2-ol. The solvent is evaporated under reduced pressure, the solid obtained is collected and is dried under reduced pressure.

0.9 g of hydrochloride is finally isolated in the form of a white solid.

Melting point: 175–185° C. $[\alpha]_D^{25} = +18.4°$ (c=0.091; $CH_3OH$) ee=97.8%.

EXAMPLE 5

(Compound No. 36)

threo-2-Chloro-N-[phenyl(piperidin-2-yl)methyl]-3-trifluoromethylbenzamide hydrochloride 1:1

5.1. 2-Chloro-N-[phenyl(pyridin-2-yl)methyl]-3-trifluoromethylbenzamide.

1.61 g (7.16 mmol) of 2-chloro-3-trifluoromethylbenzoic acid, 1.4 g (7.28 mmol) of 1-[3-(dimethylamino)propyl]-3-ethylcarbodiimide hydrochloride, 0.218 g (1.79 mmol) of 4-dimethylaminopyridine in solution in 60 ml of dichloromethane are placed in a 250 ml round-bottomed flask, the mixture is stirred for 15 min, 1.1 g (5.97 mmol) of phenyl(pyridin-2-yl)methanamine in solution in 60 ml of dichloromethane are added and the mixture is stirred at room temperature for 24 h.

It is hydrolysed by adding water, a 35% aqueous sodium hydroxide solution is added, the organic phase is separated, it is washed with water and then with a saturated aqueous sodium chloride solution, it is dried over magnesium sulphate, it is filtered and the solvent is evaporated under reduced pressure. The residue is purified by chromatography on a silica gel column, eluting with a mixture of dichloromethane and methanol, and 1.34 g of product are finally isolated in the form of a yellow oil which crystallizes, and which is used as it is in the next step.

5.2. threo-2-Chloro-N-[phenyl(piperidin-2-yl)methyl]-3-trifluoromethylbenzamide hydrochloride 1:1.

A solution of 4.17 g (10 mmol) of 2-chloro-N-[phenyl(piperidin-2-yl)methyl]-3-trifluoromethylbenzamide in 43 ml of glacial acetic acid is placed in a Parr flask, 0.1 g of 5% palladium on carbon is added and hydrogenation is performed at 0.35 MPa at 50° C. for 3 h.

After returning to room temperature, the catalyst is removed by filtration, the filtrate is concentrated under reduced pressure, the residue is taken up with water and ethyl acetate, concentrated sodium hydroxide is added and the mixture is extracted several times with ethyl acetate. The organic phase is washed with water and then with a saturated aqueous sodium chloride solution, it is dried over sodium sulphate, it is filtered and the solvent is evaporated under reduced pressure. The residue is purified by two successive chromatographies on a silica gel column, eluting with a 100/0 to 95/5 mixture of dichloromethane and methanol, in order to separate the unreacted starting material.

0.8 g of the (less polar) threo diastereoisomer is isolated. The hydrochloride thereof is prepared by dissolving it in a few ml of propan-2-ol and adding thereto 20 ml of a 0.1 N hydrochloric acid solution in propan-2-ol. The solvent is partially evaporated under reduced pressure, a white solid is obtained by trituration, it is collected by filtration and it is dried under reduced pressure.

0.6 g of hydrochloride is finally obtained.

Melting point: 234–235° C.

EXAMPLE 6

(Compound No. 37)

2-Chloro-N-[(S)-phenyl-[(2S)-piperidin-2-yl]methyl]-3-(trifluoromethyl)benzamide hydrochloride 1:1

8.36 g (3 eq.) of 1,3-dimethylbarbituric acid in solution in 100 ml of anhydrous dichloromethane are introduced into a 500 ml two-necked flask provided with magnetic stirring, with circulation of argon and with a condenser. 0.2 g (0.01 eq.) of tetrakis(triphenylphosphine)palladium is added and the reaction medium is heated to 35° C.

A solution of 7.8 g (19.18 mmol) of N-[(S)-[(2-S)-1-allylpiperidin-2-yl](phenyl)methyl]-2-chloro-3-(trifluoromethyl)benzamide (obtained according to a procedure similar to that of Example 1) is added, and the progress of the reaction is monitored by thin-layer chromatography. 100 ml of a saturated sodium hydrogen carbonate solution are added, the medium is separated after settling out and the aqueous phase is extracted twice with 100 ml of dichloromethane, the combined organic phases are washed with 100 ml of water and then with 100 ml of a saturated sodium chloride solution. They are dried over sodium sulphate, filtered and the solvent is evaporated under reduced pressure.

10.15 g of a beige solid are obtained, which solid is purified by chromatography on a silica gel column, eluting with a mixture of dichloromethane containing 0.4% of a 33% ammonia solution.

4.8 g of a whitish solid are isolated. The solid is dissolved in 50 ml of propan-2-ol and 125 ml of a 0.1 N hydrochloric acid in propan-2-ol are added and the mixture is concentrated under reduced pressure in order to reduce the volume of solvent.

After trituration, 4.33 g of hydrochloride are isolated in the form of white crystals.

Melting point: 223–225° C. $[\alpha]_D^{25} = +80.7°$ (c=0.5; $CH_3OH$) ee>98%.

EXAMPLE 7

(Compounds Nos 69 and 70)

2-Chloro-N-[[1-methyl-1-oxido-piperidin-2-yl](phenyl)methyl]-3-trifluoromethylbenzamide.

0.54 g (1.3 mmol) of threo-2-chloro-N-[(1-methylpiperidin-2-yl)phenylmethyl]-3-trifluoromethylbenzamide in 20 ml of anhydrous dichloromethane at 0° C. is introduced into a 50 ml round-bottomed flask provided with magnetic stirring, a solution of 0.28 g (1.2 eq.) of 3-chloroperbenzoic acid in 5 ml of dichloromethane is added and the mixture is allowed to return to room temperature with stirring for 12 h.

30 ml of water are added, the medium is separated after settling out and the aqueous phase is extracted twice with 30 ml of dichloromethane, the combined phases are washed with 100 ml of water and then 100 ml of a saturated sodium chloride solution. The organic phase is dried over sodium sulphate, the solvents are removed under reduced pressure and the residue is purified by chromatography on a silica gel column, eluting with a 90/10 mixture of dichloromethane and methanol over 40 min.

0.15 g of the first N-oxide isomer (melting point: 100–102° C.) and 0.03 g of the second N-oxide isomer (melting point: 126–128° C.) are isolated.

EXAMPLE 8

(Compound No. 71)

(2S)-2[(1S)-[[2-Chloro-3-(trifluoromethyl)benzoyl]amino](phenyl)methyl]-1,1-dimethylpiperidinium iodide 0.15 g (0.36 mmol) of 2-chloro-N-[(1S)-[(2S)-1-methylpiperidin-2-yl]phenylmethyl]-3-trifluoromethylbenzamide in solution in 20 ml of acetonitrile is introduced into a 50 ml two-necked flask provided with magnetic stirring, argon circulation and a condenser, 0.5 ml of iodomethane is added and the medium is heated at 80° C. for 2 h.

The reaction medium is concentrated by half, the ammonium salt precipitates, it is filtered and it is dried under reduced pressure.

0.17 g of a yellow solid is isolated. Melting point: 121–123° C.

Table 1 which follows illustrates the chemical structures of a few compounds of the invention.

In the "A" column, $cC_3H_5$ denotes a cyclopropyl group. In the "$CF_3$" column is indicated the position of the $CF_3$ group in general formula (I). In the "$R_2$" column, $C_6H_6$ denotes a phenyl group. In the "Salt" column, "-" denotes a compound in base state, "HCl" denotes a hydrochloride and "tfa" denotes a trifluoroacetate.

Table 2 illustrates the physical properties, melting points and optical rotations of a few compounds.

TABLE 1

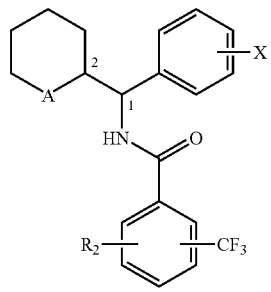

(I)

| No. | Stereochemistry | A | X | $CF_3$ | $R_2$ | Salt |
|---|---|---|---|---|---|---|
| 1 | threo (1R,2R;1S,2S) | N-$CH_3$ | H | 6 | 2-F, 3-Cl | HCl |
| 2 | threo (1R,2R;1S,2S) | N-$CH_3$ | H | 2 | 4-$CF_3$ | HCl |
| 3 | threo (1R,2R;1S,2S) | N-$CH_3$ | H | 2 | 6-$CF_3$ | HCl |
| 4 | threo (1R,2R;1S,2S) | N-$CH_3$ | H | 2 | 5-Cl | HCl |
| 5 | threo (1R,2R;1S,2S) | N-$CH_3$ | H | 2 | 4-F | — |
| 6 | threo (1R,2R;1S,2S) | N-$CH_3$ | H | 2 | 5-$CF_3$ | — |
| 7 | threo (1R,2R;1S,2S) | N-$CH_3$ | H | 2 | 3-Cl | HCl |
| 8 | threo (1R,2R;1S,2S) | N-$CH_3$ | H | 4 | 2,6-$Cl_2$ | HCl |
| 9 | threo (1R,2R;1S,2S) | N-$CH_3$ | H | 4 | 2-Cl | HCl |
| 10 | threo (1R,2R;1S,2S) | N-$CH_3$ | H | 4 | 3-Cl | HCl |
| 11 | threo (1R,2R;1S,2S) | N-$CH_3$ | H | 3 | 4-F | HCl |
| 12 | threo (1R,2R;1S,2S) | N-$CH_3$ | H | 3 | H | HCl |
| 13 | threo (1R,2R;1S,2S) | N-$CH_3$ | H | 5 | 2-Cl | HCl |
| 14 | (1S,2S) | N-$CH_3$ | H | 5 | 2-Cl | HCl |
| 15 | (1R,2R) | N-$CH_3$ | H | 5 | 2-Cl | HCl |
| 16 | threo (1R,2R;1S,2S) | N-$CH_3$ | H | 3 | 5-$CF_3$ | HCl |
| 17 | threo (1R,2R;1S,2S) | N-$CH_3$ | H | 3 | 2-Cl | HCl |
| 18 | (1S,2S) | N-$CH_3$ | H | 3 | 2-Cl | HCl |
| 19 | (1R,2R) | N-$CH_3$ | H | 3 | 2-Cl | HCl |
| 20 | threo (1R,2R;1S,2S) | N-$CH_3$ | H | 3 | 4-Cl | HCl |
| 21 | threo (1R,2R;1S,2S) | N-$CH_3$ | H | 5 | 2-F, 3-Cl | — |
| 22 | threo (1R,2R;1S,2S) | N-$CH_3$ | H | 5 | 2-F | — |
| 23 | threo (1R,2R;1S,2S) | N-$CH_3$ | H | 5 | 2-$OCH_3$, 4-$C_6H_5$ | HCl |
| 24 | threo (1R,2R;1S,2S) | N-$CH_3$ | H | 5 | 3-Cl, 4-$NH_2$ | HCl |
| 25 | (1R,2R) | N-$CH_3$ | H | 5 | 3-Cl, 4-$NH_2$ | HCl |
| 26 | threo (1R,2R;1S,2S) | N-$CH_3$ | 2-$CH_3$ | 3 | 2-Cl | HCl |

TABLE 1-continued

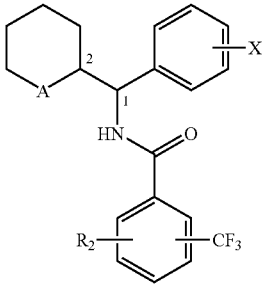

| No. | Stereochemistry | A | X | $CF_3$ | $R_2$ | Salt |
|---|---|---|---|---|---|---|
| 27 | threo (1R,2R;1S,2S) | N-$CH_3$ | H | 3 | 2,6-$Cl_2$ | HCl |
| 28 | (1S,2S) | N-$CH_3$ | H | 3 | 2,6-$Cl_3$ | HCl |
| 29 | threo (1R,2R;1S,2S) | N-$CH_3$ | 4-F | 3 | 2-Cl | HCl |
| 30 | (1S,2S) | N-$CH_3$ | 4-F | 3 | 2-Cl | HCl |
| 31 | (1S,2S) | N-$CH_3$ | 4-Cl | 3 | 2-Cl | HCl |
| 32 | (1S,2S) | N-$CH_3$ | 4-C($CH_3$)$_3$ | 3 | 2-Cl | tfa |
| 33 | threo (1R,2R;1S,2S) | N-$CH_2CH_3$ | H | 3 | 2-Cl | HCl |
| 34 | (1S,2S) | N-$CH_3$ | 4-$CH_3$ | 3 | 2-Cl | HCl |
| 35 | threo (1R,2R;1S,2S) | N-$CH_3$ | H | 2 | 4-Cl | HCl |
| 36 | threo (1R,2R;1S,2S) | NH | H | 3 | 2-Cl | HCl |
| 37 | (1S,2S) | NH | H | 3 | 2-Cl | HCl |
| 38 | (1R,2R) | NH | H | 3 | 2-Cl | HCl |
| 39 | threo (1R,2R;1S,2S) | N-$CH_2CH(CH_3)_2$ | H | 3 | 2-Cl | HCl |
| 40 | (1S,2S) | N-$CH_2CH(CH_3)_2$ | H | 3 | 2-Cl | HCl |
| 41 | threo (1R,2R;1S,2S) | N-$(CH_2)_2CH_3$ | H | 3 | 2-Cl | HCl |
| 42 | (1S,23) | N-$(CH_2)_2CH_3$ | H | 3 | 2-Cl | HCl |
| 43 | (1S,2S) | N-$CH_2cC_3H_5$ | H | 3 | 2-Cl | HCl |
| 44 | threo (1R,2R;1S,2S) | N-$CH_3$ | H | 3 | 2-$CH_3$ | HCl |
| 45 | (1S,2S) | N-$CH(CH_3)_2$ | H | 3 | 2-Cl | HCl |
| 46 | (1S,2S) | N-$(CH_2)_3CH_3$ | H | 3 | 2-Cl | HCl |
| 47 | (1S,2S) | N-$CH_2$=CH | H | 3 | 2-Cl | HCl |
| 48 | (1S,2S) | N-$CH_2C_6H_5$ | H | 3 | 2-Cl | HCl |
| 49 | (1S,2S) | H-$CH_2$[3,4-$(OCH_3)_2C_6H_3$] | H | 3 | 2-Cl | — |
| 50 | threo (1R,2R;1S,2S) | N-$CH_3$ | H | 5 | 2-$CH_3$ | |
| 51 | threo (1R,2R;1S,2S) | N-$(CH_2)_3CF_3$ | H | 3 | 2-Cl | HCl |
| 52 | (1S,2S) | N-$(CH_2)_3CH_3$ | H | 3 | 2-$CH_3$ | HCl |
| 53 | threo (1R,2R;1S,2S) | N-$(CH_2)_3CH_3$ | 4-F | 3 | 2-$CH_3$ | HCl |
| 54 | threo (1R,2R;1S,2S) | N-$(CH_2)_3CH_3$ | 4-F | 3 | 2-Cl | HCl |
| 55 | threo (1R,2R;1S,2S) | N-$(CH_2)_3CH_3$ | 4-Cl | 3 | 2-Cl | HCl |
| 56 | threo (1R,2R;1S,2S) | N-$(CH_2)_3CH_3$ | 4-Cl | 3 | 2-$CH_3$ | HCl |
| 57 | (1S,2S) | N-$CH_3$ | H | 3 | 2-$CH_3$ | HCl |
| 58 | (1S,2S) | N-$(CH_2)_3CH_3$ | 4-F | 3 | 2-Cl | HCl |
| 59 | threo (1R,2R;1S,2S) | N-$CH_2CH$=$CH_2$ | H | 3 | 2-Cl | HCl |
| 60 | (1S,2S) | N-$CH_2CH$=$CH_2$ | H | 3 | 2-Cl | HCl |
| 61 | (1S,2S) | NH | H | 3 | 2-$CH_3$ | HCl |
| 62 | (1S,2S) | NH | H | 6 | 2-F, 3-Cl | HCl |
| 63 | (1S,2S) | NH | H | 5 | 2-Cl | HCl |
| 64 | threo (1R,2R;1S,2S) | NH | H | 2 | 4-$CF_3$ | HCl |
| 65 | threo (1R,2R;1S,2S) | NH | H | 3 | H | HCl |
| 66 | threo (1R,2R;1S,2S) | NH | H | 3 | 2-F | HCl |
| 67 | threo (1R,2R;1S,2S) | NH | H | 3 | 5-$CF_3$ | HCl |
| 68 | threo (1R,2R;1S,2S) | NH | H | 2 | 5-$CF_3$ | HCl |
| 69 | threo (1R,2R;1S,2S) | $N^+(O^-)CH_3$ | H | 3 | 2-Cl | HCl |
| 70 | threo (1R,2R;1S,2S) | $N^+(O^-)CH_3$ | H | 3 | 2-Cl | HCl |
| 71 | (1S,2S) | $N^+(CH_3)_2$ | H | 3 | 2-Cl | HCl |

Compound No. 69: the most polar diastereoisomer
Compound No. 70: the least polar diastereoisomer

TABLE 2

| No. | m.p. (° C.) | $[\alpha]_D^{25}$ |
|---|---|---|
| 1 | >270 | — |
| 2 | 152–154 | — |
| 3 | >285 | — |
| 4 | 275–276 | — |
| 5 | 51–52 | — |
| 6 | 169 | — |
| 7 | 228–229 | — |
| 8 | 287–288 | — |
| 9 | 84–86 | — |
| 10 | 187–191 | — |
| 11 | 237.5–238.5 | — |
| 12 | 174–176 | — |
| 13 | 229–231 | — |
| 14 | 95–100 | +67.7 (c = 0.26; $CH_3OH$) |

TABLE 2-continued

| No. | m.p. (° C.) | $[\alpha]_D^{25}$ |
|---|---|---|
| 15 | 95–100 | −66.5 (c = 0.275; CH$_3$OH) |
| 16 | 200–201.5 | — |
| 17 | 215–216 | — |
| 18 | 230–232 | +70.7 (c = 0.825; CH$_3$OH) |
| 19 | 243–248 | −74.26 (c = 0.715; CH$_3$OH) |
| 20 | 225–227 | — |
| 21 | 150–151 | — |
| 22 | 196–197 | — |
| 23 | 153–154 | — |
| 24 | 270–272 | — |
| 25 | 175–185 | +18.4 (c = 0.091; CH$_3$OH) |
| 26 | 277–279 | — |
| 27 | 297–300 | — |
| 28 | 260–262 | +50.53 (c = 0.56; CH$_3$OH) |
| 29 | 109–111 | — |
| 30 | 236–238 | +50.23 (c = 0.325; CH$_3$OH) |
| 31 | 238–240 | — |
| 32 | 95–97 | — |
| 33 | 230–232 | — |
| 34 | 222–224 | +70.9 (c = 0.573; CH$_3$OH) |
| 35 | 258–259 | — |
| 36 | 234–235 | — |
| 37 | 223–225 | +80.7 (c = 0.5; CH$_3$OH) |
| 38 | 217–219 | −74.2 (c = 0.51; CH$_3$OH) |
| 39 | 158–160 | — |
| 40 | 80–82 | +67.3 (c = 0.854; CH$_3$OH) |
| 41 | 124–126 | — |
| 42 | 210–212 | +80.7 (c = 0.896; CH$_3$OH) |
| 43 | 200–202 | +71.7 (c = 0.882; CH$_3$OH) |
| 44 | 259–260 | — |
| 45 | 256–258 | +18.1 (c = 1; CH$_3$OH) |
| 46 | 200–202 | +79.7 (c = 0.798; CH$_3$OH) |
| 47 | 79–81 | — |
| 48 | 216–218 | +66.4 (c = 1; CH$_3$OH) |
| 49 | 132 | |
| 50 | 256–257 | |
| 51 | 162–164 | |
| 52 | 101–103 | +57.9 (c = 0.87; CH$_3$OH) |
| 53 | 234–236 | |
| 54 | 110–112 | |
| 55 | 199–201 | |
| 56 | 94–96 | |
| 57 | 141–143 | +56.3 (c = 0.59; CH$_3$OH) |
| 58 | 224–226 | +74.90 (c = 0.66; CH$_3$OH) |
| 59 | 138–140 | |
| 60 | 104–106 | +78.5 (c = 0.57; CH$_3$OH) |
| 61 | 214–216 | +54.8 (c = 0.2; CH$_3$OH) |
| 62 | 135–137 | +86.3 (c = 0.5; CH$_3$OH) |
| 63 | 194–196 | +61.5 (c = 0.5; CH$_3$OH) |
| 64 | 149–151 | |
| 65 | 199–201 | |
| 66 | 221–223 | |
| 67 | 167–169 | |
| 68 | 255–257 | |
| 69 | 126–128 | |
| 70 | 100–102 | |
| 71 | 121–123 | |

The compounds of the invention were subjected to a series of pharmacological trials which demonstrated their importance as substances with therapeutic activity.

Study of the Transport of Glycine in SK-N-MC Cells Expressing the Native Human Transporter glyt1

The capture of [$^{14}$C]glycine is studied in SK-N-MC cells (human neuroepithelial cells) expressing the native human transporter glyt1 by measuring the radioactivity incorporated in the presence or in the absence of the test compound. The cells are cultured in a monolayer for 48 h in plates pretreated with fibronectin at 0.02%. On the day of the experiment, the culture medium is removed and the cells are washed with a Krebs-HEPES ([4-(2-hydroxyethyl)piperazine-1-ethanesulphonic acid) buffer at pH 7.4. After a preincubation of 10 min at 37° C. in the presence either of buffer (control batch), or of test compound at various concentrations, or of 10 mM glycine (determination of the nonspecific capture), 10 µM [$^{14}$C]glycine (specific activity 112 mCi/mmol) are then added. The incubation is continued for 10 min at 37° C., and the reaction is stopped by 2 washes with a Krebs-HEPES buffer at pH 7.4. The radioactivity incorporated by the cells is then estimated after adding 100 µl of liquid scintillant and stirring for 1 h. The counting is performed on a Microbeta Tri-lux™ counter. The efficacy of the compound is determined by the IC$_{50}$, the concentration of the compound which reduces by 50% the specific capture of glycine, defined by the difference in radioactivity incorporated by the control batch and the batch which received the glycine at 10 mM.

The compounds of the invention, in this test, have an IC$_{50}$ of the order of 0.0001 to 10 µM.

Study Ex Vivo of the Inhibitory Activity of a Compound on the Capture of [$^{14}$C]Glycine in Mouse Cortical Homogenate Increasing doses of the compound to be studied are administered by the oral route (preparation by trituration of the test molecule in a mortar in a solution of Tween/Methocel™ at 0.5% in distilled water) or by the intraperitoneal route (dissolution of the test molecule in physiological saline or preparation by trituration in a mortar in a solution of Tween/Methocel™ at 0.5% in water, according to the solubility of the molecule) to 20 to 25 g Iffa Crédo OF1 male mice on the day of the experiment. The control group is treated with the vehicle. The doses in mg/kg, the route of administration and the treatment time are determined according to the molecule to be studied.

After the animals have been humanely killed by decapitation at a given time after the administration, the cortex of each animal is rapidly removed on ice, weighed and stored at 4° C. or frozen at −80° C. (in both cases, the samples are stored for a maximum of 1 day). Each sample is homogenized in a Krebs-HEPES buffer at pH 7.4 at a rate of 10 ml/g of tissue. 20 µl of each homogenate are incubated for 10 min at room temperature in the presence of 10 mM L-alanine and buffer. The nonspecific capture is determined by adding 10 mM glycine to the control group. The reaction is stopped by filtration under vacuum and the retained radioactivity is estimated by solid scintillation by counting on a Microbeta Tri-lux™ counter.

An inhibitor of the capture of [$^{14}$C]glycine will reduce the quantity of radioligand incorporated into each homogenate. The activity of the compound is evaluated by its ED$_{50}$, the dose which inhibits by 50% the capture of [$^{14}$C]glycine compared with the control group.

The most potent compounds of the invention, in this test, have an ED$_{50}$ of 0.1 to 5 mg/kg by the intraperitoneal route or by the oral route.

Study of the Transport of Glycine in Mouse Spinal Cord Homogenate

The capture of [$^{14}$C]glycine by the transporter glyt2 is studied in mouse spinal cord homogenate by measuring the radioactivity incorporated in the presence or in the absence of the compound to be studied.

After the animals have been humanely killed (Iffa Crédo OF1 male mice weighing 20 to 25 g on the day of the experiment), the spinal cord of each animal is rapidly removed, weighed and stored on ice. The samples are homogenized in a Krebs-HEPES ([4-(2-hydroxyethyl)piperazine-1-ethanesulphonic acid) buffer, pH 7.4, at a rate of 25 ml/g of tissue.

50 µl of homogenate are preincubated for 10 min at 25° C. in the presence of Krebs-HEPES buffer, pH 7.4 and of compound to be studied at various concentrations, or of 10 mM glycine in order to determine the nonspecific capture. The [$^{14}$C]glycine (specific activity=112 mCi/mmol) is then added for 10 min at 25° C. at the final concentration of 10 µM. The reaction is stopped by filtration under vacuum and the radioactivity is estimated by solid scintillation by counting on a Microbeta Tri-lux™ counter. The efficacy of the compound is determined by the concentration $IC_{50}$ capable of reducing by 50% the specific capture of glycine, defined by the difference in radioactivity incorporated by the control batch and the batch which received the 10 mM glycine.

The compounds of the invention in this test have an $IC_{50}$ of the order of 0.0001 to 10 µM.

Study Ex Vivo of the Inhibitory Activity of a Compound on the Capture of [$^{14}$C]Glycine in Mouse Spinal Homogenate Increasing doses of the compound to be studied are administered by the oral route (preparation by trituration of the test compound in a mortar, in a solution of Tween/Methocel™ at 0.5% in distilled water) or intraperitoneal route (test compound dissolved in physiological saline, or triturated in a mortar, in a solution of Tween/Methocel™ at 0.5% in distilled water) to 20 to 25 g Iffa Crédo OF1 male mice on the day of the experiment. The control group is treated with the vehicle. The doses in mg/kg, the route of administration, the treatment time and the humane killing time are determined according to the compound to be studied.

After humanely killing the animals by decapitation at a given time after the administration, the spinal cords are rapidly removed, weighed and introduced into glass scintillation bottles, stored on crushed ice or frozen at −80° C. (in both cases, the samples are stored for a maximum of 1 day). Each sample is homogenized in a Krebs-HEPES buffer at pH 7.4, at a rate of 25 ml/g of tissue. 50 µl of each homogenate are incubated for 10 min at room temperature in the presence of buffer.

The nonspecific capture is determined by adding 10 mM glycine to the control group.

The reaction is stopped by filtration under vacuum and the radioactivity is estimated by solid scintillation by counting on a Microbeta Tri-lux™ counter.

An inhibitor of the capture of [$^{14}$C]glycine will reduce the quantity of radioligand incorporated in each homogenate. The activity of the compound is evaluated by its $ED_{50}$, the effective dose which inhibits by 50% the capture of [$^{14}$C] glycine compared with the control group.

The best compounds of the invention have, in this test, an $ED_{50}$ of 1 to 20 mg/kg, by the intraperitoneal route or by the oral route.

The results of the trials carried out on the compounds of the invention having the configuration (1S,2S) and their threo racemates having the configuration (1R,2R; 1S,2S) in the general formula (I) of which $R_2$ represents one or more halogen atoms or trifluoromethyl groups show that they are inhibitors of the glycine transporter glyt1 which are present in the brain, this being in vitro and ex vivo.

These results suggest that the compounds of the invention can be used for the treatment of behavioural disorders associated with dementia, psychoses, in particular schizophrenia (deficient form and productive form) and acute or chronic extrapyramidal symptoms induced by neuroleptics, for the treatment of various forms of anxiety, panic attacks, phobias, obsessive-compulsive disorders, for the treatment of various forms of depression, including psychotic depression, for the treatment of disorders due to alcohol abuse or to withdrawal from alcohol, sexual behaviour disorders, food intake disorders, and for the treatment of migraine.

The results of the trials carried out on the compounds of the invention having the configuration (1R,2R) and their racemates having the configuration (1R,2R; 1S,2S) in the general formula (I) of which $R_2$ represents both a halogen atom and an amino group $NR_3R_4$ show that they are inhibitors of the glycine transporter glyt2, predominantly present in the spinal cord, this being in vitro and ex vivo.

These results suggest that the compounds of the invention may be used for the treatment of painful muscular contractures in rheumatology and in acute spinal pathology, for the treatment of spastic contractures of medullary or cerebral origin, for the symptomatic treatment of acute and subacute pain of mild to moderate intensity, for the treatment of intense and/or chronic pain, of neurogenic pain and rebellious algia, for the treatment of Parkinson's disease and of Parkinsonian symptoms of neurodegenerative origin or induced by neuroleptics, for the treatment of primary and secondary generalized epilepsy, partial epilepsy with a simple or complex symptomatology, mixed forms and other epileptic syndromes as a supplement to another antiepileptic treatment, or in monotherapy, for the treatment of sleep apnoea, and for neuroprotection.

Accordingly, the subject of the present invention is also pharmaceutical compositions containing an effective dose of at least one compound according to the invention, in the form of a pharmaceutically acceptable base or salt or solvate, and in the form of a mixture, where appropriate, with suitable excipients.

The said excipients are chosen according to the pharmaceutical dosage form and the desired mode of administration.

The pharmaceutical compositions according to the invention may thus be intended for oral, sublingual, subcutaneous, intramuscular, intravenous, topical, intratracheal, intranasal, transdermal, rectal or intraoccular administration.

The unit forms for administration may be, for example, tablets, gelatin capsules, granules, powders, oral or injectable solutions or suspensions, patches or suppositories. For topical administration, it is possible to envisage ointments, lotions and collyria.

The said unit forms contain doses in order to allow a daily administration of 0.01 to 20 mg of active ingredient per kg of body weight, according to the galenic form.

To prepare tablets, there are added to the active ingredient, micronized or otherwise, a pharmaceutical vehicle which may be composed of diluents, such as for example lactose, microcrystalline cellulose, starch, and formulation adjuvants such as binders, (polyvinylpyrrolidone, hydroxypropylmethylcellulose, and the like), flow-enhancing agents such as silica, lubricants such as magnesium stearate, stearic acid, glyceryl tribehenate, sodium stearylfumarate. Wetting agents or surfactants, such as sodium lauryl sulphate, may also be added.

The techniques for production may be direct compression, dry granulation, wet granulation or hot-melt.

The tablets may be uncoated, coated, for example with sucrose, or coated with various polymers or other appropriate materials. They may be designed to allow rapid, delayed or prolonged release of the active ingredient by virtue of polymer matrices or specific polymers used in the coating.

To prepare gelatin capsules, the active ingredient is mixed with dry (simple mixture, dry or wet granulation, or hot-melt), liquid or semisolid pharmaceutical vehicles.

The gelatin capsules may be hard or soft, film-coated or otherwise, so as to have rapid, prolonged or delayed activity (for example for an enteric form).

A composition in syrup or elixir form or for administration in the form of drops may contain the active ingredient together with a sweetener, preferably calorie-free, methylparaben or propylparaben as antiseptic, a flavour modifier and a colouring.

The water-dispersible powder and granules may contain the active ingredient in the form of a mixture with dispersing agents or wetting agents, or dispersants such as polyvinylpyrrolidone, and with sweeteners and flavour corrigents.

For rectal administration, suppositories are used which are prepared with binders which melt at rectal temperature, for example cocoa butter or polyethylene glycols.

For parenteral administration, there are used aqueous suspensions, isotonic saline solutions or sterile solutions for injection containing pharmacologically compatible dispersing agents and/or wetting agents, for example propylene glycol or butylene glycol.

The active ingredient may also be formulated in the form of microcapsules, optionally with one or more carriers or additives, or alternatively with a polymer matrix or with a cyclodextrin (patches, prolonged release forms).

The topical compositions according to the invention comprise a medium compatible with the skin. They may be provided in particular in the form of aqueous, alcoholic or aqueous-alcoholic solutions, gels, water-in-oil or oil-in-water emulsions having the appearance of a cream or of a gel, microemulsions, aerosols, or alternatively in the form of vesicular dispersions containing ionic and/or nonionic lipids. These galenic forms are prepared according to the customary methods in the fields considered.

Finally, the pharmaceutical compositions according to the invention may contain, apart from a compound of general formula (I), other active ingredients which may be useful in the treatment of the disorders and diseases indicated above.

What is claimed is:

1. A compound in the form of an enantiomer (1R,2R) or (1S,2S) or in the form of a threo diastereoisomer, corresponding to general formula (I)

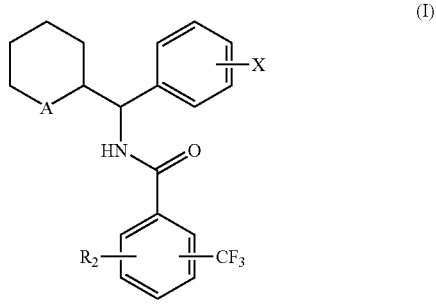

(I)

in which A represents
a group of general formula N—$R_1$, a group of general formula $N^+(O^-)R_1$ or a group of general formula $N^+(R')R_1$, and in which $R_1$ represents either a hydrogen atom, or a linear or branched ($C_1$–$C_7$)alkyl group optionally substituted with one or more fluorine atoms, or a ($C_4$–$C_7$)cycloalkyl group, or a ($C_3$–$C_7$)cycloalkyl ($C_1$–$C_3$)alkyl group, or a phenyl($C_1$–$C_3$)alkyl group optionally substituted with one or two hydroxyl or methoxy groups, or a ($C_2$–$C_4$)alkenyl group, or a ($C_2$–$C_4$)alkynyl group, R' represents a linear or branched ($C_1$–$C_7$)alkyl group,
X represents a hydrogen atom or one or more substituents chosen from halogen atoms and trifluoromethyl, linear or branched ($C_1$–$C_4$)alkyl and ($C_1$–$C_4$)alkoxy groups,
$R_2$ represents either a hydrogen atom, or one or more substituents chosen from halogen atoms and trifluoromethyl, ($C_1$–$C_4$)alkyl or ($C_1$–$C_4$)alkoxy groups, or amino groups of general formula $NR_3R_4$ in which $R_3$ and $R_4$ each represent, independently of each other, a hydrogen atom or a ($C_1$–$C_4$)alkyl group, or form with the nitrogen atom carrying them a pyrrolidine, piperidine or morpholine ring, or a phenyl group optionally substituted with an atom or a group as defined for the symbol X above,
in the form of a free base or of an addition salt with an acid.

2. A compound according to claim 1 wherein it has the configuration (1S,2S) and in that $R_2$ represents one or more halogen atoms or trifluoromethyl groups.

3. A compound according to claim 1 wherein it has the configuration (1R,2R) and in that $R_2$ represents a halogen atom and an amino group of general formula $NR_3R_4$ as defined in claim 1.

4. A compound according to claim 1 wherein A represents a group of general formula N—$R_1$ in which $R_1$ represents either a hydrogen atom, or a linear or branched ($C_1$–$C_7$)alkyl group optionally substituted with one or more fluorine atoms and said compound in the form of a free base or of an addition salt with an acid.

5. A compound according to claim 1 which is selected from the group consisting of:
threo-2-chloro-N-[(1-ethylpiperidin-2-yl)phenylmethyl]-3-trifluoromethylbenzamide hydrochloride;
threo-2-chloro-N-[(1-ethylpiperidin-2-yl)phenylmethyl]-3-trifluoromethylbenzamide;
2-chloro-N-[(1S)-[(2S)-1-methylpiperidin-2-yl]phenylmethyl]-3-trifluoromethyl -benzamide hydrochloride;
2-chloro-N-[(1S)-[(2S)-1-methylpiperidin-2-yl]phenylmethyl]-3-trifluoromethyl-benzamide;
threo-4-amino-3-chloro-N-[(1-methylpiperidin-2-yl)phenylmethyl]-5-trifluoromethyl-benzamide hydrochloride;
threo-4-amino-3-chloro-N-[(1-methylpiperidin-2-yl)phenylmethyl]-5-trifluoromethyl-benzamide;
4-amino-3-chloro-N-[(1R)-[(2R)-1-methylpiperidin-2-yl]phenylmethyl]-5-trifluoro -methylbenzamide hydrochloride;
4-amino-3-chloro-N-[(1R)-[(2R)-1-methylpiperidin-2-yl]phenylmethyl]-5-trifluoro -methylbenzamide;
threo-2-chloro-N-[phenyl(piperidin-2-yl)methyl]-3-trifluoromethylbenzamide hydrochloride;
threo-2-chloro-N-[phenyl(piperidin-2-yl)methyl]-3-trifluoromethylbenzamide;
2-chloro-N-[(S)-phenyl-[(2S)-piperidin-2-yl]methyl]-3-(trifluoromethyl)benzamide hydrochloride;
2-chloro-N-[(S)-phenyl-[(2S)-piperidin-2-yl]methyl]-3-(trifluoromethyl)benzamide;
2-chloro-N-[[1-methyl-1-oxido-piperidin-2-yl](phenyl)methyl]-3-trifluoromethyl -benzamide; and
2(S)-2[(1S)-[[2-chloro-3-(trifluoromethyl)benzoyl]amino](phenyl)methyl]-1,1-dimethylpiperidinium iodide or
a pharmaceutically acceptable salt thereof.

6. 2-Chloro-N-[(S)-phenyl-[(2S)-piperidin-2-yl]methyl]-3-(trifluoromethyl)benzamide according to claim 1.

7. 2-Chloro-N-[(S)-phenyl-[(2S)-piperidin-2-yl]methyl]-3-(trifluoromethyl)benzamide hydrochloride 1:1 according to claim 6.

8. 2-chloro-N-[(1S)-[(2S)-1-methylpiperidin-2-yl]phenylmethyl]-3-trifluoromethylbenzamide according to claim 1.

9. 2-chloro-N-[(1S)-[(2S)-1-methylpiperidin-2-yl]phenylmethyl]-3-trifluoromethylbenzamide hydrochloride 1:1 according to claim 1.

10. 4-amino-3-chloro-N-[(1R)-[(2R)-1-methylpiperidin-2-yl]phenylmethyl]-5-trifluoromethylbenzamide hydrochloride 1:1 according to claim 1.

11. A Pharmaceutical composition comprising a compound according to claim 1 combined with an excipient.

12. A pharmaceutical composition comprising a compound according to claim 2 combined with an excipient.

13. A pharmaceutical composition comprising a compound according to claim 3 combined with an excipient.

14. A pharmaceutical composition comprising a compound according to claim 6 combined with an excipient.

15. A pharmaceutical composition comprising a compound according to claim 7 combined with an excipient.

16. A pharmaceutical composition comprising a compound according to claim 5 combined with an excipient.

17. A pharmaceutical composition comprising a compound according to claim 8 combined with an excipient.

18. A pharmaceutical composition comprising a compound according to claim 9 combined with an excipient.

19. A pharmaceutical composition comprising a compound according to claim 10 combined with an excipient.

* * * * *